(12) United States Patent
Hu et al.

(10) Patent No.: US 9,629,385 B2
(45) Date of Patent: Apr. 25, 2017

(54) **DIETARY COMPOSITION CONTAINING *CISTANCHE DESERTICOLA* POLYSACCHARIDE WITH INHIBITORY EFFECTS ON COLON CANCER**

(71) Applicant: Huisen Li, Jiangmen (CN)

(72) Inventors: Minghua Hu, Guangzhou (CN); Peipei Wang, Guangzhou (CN); Fangli Ma, Guangzhou (CN); Ming Liang, Guangzhou (CN)

(73) Assignee: Infinitus (China) Company Ltd., Jiangmen (CN)

( * ) Notice: Subject to any disclaimer, the term of this patent is extended or adjusted under 35 U.S.C. 154(b) by 0 days.

(21) Appl. No.: 14/615,439

(22) Filed: Feb. 6, 2015

(65) Prior Publication Data

US 2016/0227829 A1  Aug. 11, 2016

(51) Int. Cl.
*A61K 31/715* (2006.01)
*A61K 36/64* (2006.01)
*A23L 1/308* (2006.01)

(52) U.S. Cl.
CPC ............ *A23L 1/308* (2013.01); *A61K 31/715* (2013.01); *A61K 36/64* (2013.01); *A23V 2002/00* (2013.01)

(58) Field of Classification Search
CPC .............................. A61K 31/715; A23L 1/308
See application file for complete search history.

(56) References Cited

FOREIGN PATENT DOCUMENTS

CN    101870742 A  * 10/2010  ............. C08B 37/00

OTHER PUBLICATIONS

Jia et al., Phytother. Res., 2012, 26, p. 812-819.*
Machine translation of Patent CN101870742A, Google Patents, https://www.google.com/?tbm=pts&hl=en, accessed online on Jun. 15, 2016.*

* cited by examiner

*Primary Examiner* — Jonathan S Lau
(74) *Attorney, Agent, or Firm* — Bei & Ocean; George G. Wang

(57) ABSTRACT

The use of a *Cistanche deserticola* polysaccharide in the preparation of food supplement having the efficacy of inhibiting colon cancer, wherein *Cistanche deserticola* polysaccharide is prepared by a processes including extraction with boiling water, deproteinization, dialysis and ethanol treatment, and has an effect of regulating tumor microenvironment by many pathways involving inhibiting tumor angiogenesis, immunosuppression, anti-oxidation and inhibiting colon cancer fibroblasts.

5 Claims, 5 Drawing Sheets

US 9,629,385 B2

DIETARY COMPOSITION CONTAINING *CISTANCHE DESERTICOLA* POLYSACCHARIDE WITH INHIBITORY EFFECTS ON COLON CANCER

FIELD OF THE INVENTION

The present invention relates to the technical field of polysaccharide, specifically relating to the use of a *Cistanche deserticola* polysaccharide in the preparation of functional food having efficacy of inhibiting colon cancer.

BACKGROUND OF THE INVENTION

Researches of negative immunoregulation provide a new strategy for tumor treatment. In the tumor microenvironment, there exists a large amount of negative regulatory cells, which interact with and affect each other, accompanied with the co-evolution of tumor cell and microenvironment. Due to the change of immunogenicity and abnormal growth of tumor cells, fibroblasts are stimulated to release inflammatory factors, antigen-presenting cell deliver tumor antigen signal, to co-recruit immune cells to infiltrate into local tumor, and the abnormal proliferation of tumor cells causes the press on adjacent cells, causes tissue injury such as ischemic necrosis, producing a large amount of inflammatory factors, thus local tumor is in an uncontrolled inflammatory status, resulting in the generation of negative immunoregulation in the microenvironment, inducing the formation of cancer-associated fibroblast (CAF) and myeloid-derived suppressor cells (MDSC), IL10 and TGF-β induces macrophages to transform from killer M1 type into immunosuppressive M2 type; regulatory T cell is increased in the local tumor significantly. The result is inhibiting the activities of cytotoxic T cell (CTL), natural killer cell (NK), maintaining immunological tolerance status in the local tumor.

Researches in recent years show that, polysaccharide has a significant anti-tumor activity and has a rather small toxic side effect on human body, the study on the biological activity of polysaccharide has become the hotspot of research of experts and scholars at home and abroad in the medical field. Recent years, some polysaccharides and complex thereof are discovered as having significant efficacies on many diseases, such as immune disorders, cancer, diabetes, hypertension, hepatitis, blood clots, pneumonia, virus, and involving to the regulation of various living phenomena in the cell.

*Cistanche deserticola* belongs to endangered species in Orobanchaceae, is distributed in Inner Mongolia, Ningxia, Gansu and Xinjiang, and known as "desert ginseng", it has a very high medicinal value, is the traditional rare and precious Chinese medicinal herbs in China, and is also one of the most frequently used tonic medicines in the Kidney-supplementing and Yang-invigorating prescription. Nowadays, there is not use of *Cistanche deserticola* as raw material to prepare polysaccharide, and use for preparing dietary supplement having effect of inhibiting colon cancer.

SUMMARY OF THE INVENTION

The purpose of present invention is to provide the use of a *Cistanche deserticola* polysaccharide in the preparation of functional food having efficacy of supplementary for inhibiting colon cancer.

Wherein the efficacy of supplementary for inhibiting colon cancer refers to regulating tumor microenvironment by the effects of inhibiting tumor angiogenesis, immunosuppression, anti-oxidation and inhibiting the growth of colon cancer fibroblast, to achieve the efficacy of supplementary for inhibiting colon cancer tumor.

Being an embodiment of the present invention, the *Cistanche deserticola* polysaccharide according to the present invention is preferably prepared by the following method: with *Cistanche deserticola* as raw material, prepared by the processes including extraction with boiling water, deproteinization, dialysis and ethanol treatment, the *Cistanche deserticola* polysaccharide has an effect of regulating tumor microenvironment.

Being a preferable embodiment of the present invention, the *Cistanche deserticola* polysaccharide according to the present invention is specifically prepared by the following method: with *Cistanche deserticola* as raw material, after extraction with boiling water for many times, the extract liquid are combined, the extract liquid is concentrated to obtain concentrate liquid, trichloroacetic acid aqueous solution is added to the concentrate liquid to perform deproteinization treatment, after deproteinization, the reaction liquid is processed with neutralization, bag-sealed dialysis treatment, the reaction liquid in the dialysis bag is concentrated, centrifuged, ethanol is added to the supernatant to carry on ethanol precipitation, dried, then *Cistanche deserticola* polysaccharide is obtained.

In the preparation process of the *Cistanche deserticola* polysaccharide of the present invention, the specific parameter of each step is preferably as follows:

During extraction with boiling water, extraction is carried out for 1-5 times, the administration amount of boiling water during each extraction is 10-20 folds of the total mass of *Cistanche deserticola*, the duration of each extraction is 1.5-5 h.

During extraction with boiling water, the administration amount of boiling water is preferably 5-20 folds of the total mass of *Cistanche deserticola*, extraction is preferably carried out for 3 times, wherein during the first extraction, the administration amount of boiling water is preferably 10-20 folds of the total mass of raw material *Cistanche deserticola*, extraction is carried out for 2-5 h; during the second extraction, the administration amount of boiling water is preferably 10-20 folds of the total mass of raw material *Cistanche deserticola*, extraction is carried out for 1.5-5 h; during the third extraction, the administration amount of boiling water is preferably 10-20 folds of the total mass of raw material *Cistanche deserticola*, extraction is carried out for 1.5-5 h.

The extract liquid is preferably concentrated to around 1/10 of the total volume of the original extract liquid to obtain concentrate liquid.

The mass percentage content of the trichloroacetic acid aqueous solution according to the present invention is preferably 35%, the duration of deproteinization treatment is preferably 3-6 h, the volume of trichloroacetic acid aqueous solution is preferably the same as the volume of concentrate liquid.

During neutralization treatment, it is possible to use the sodium hydroxide aqueous solution with a mass percentage content of 10%.

During bag-sealed dialysis treatment, dialysis treatment is carried out preferably by using the dialysis bag with a cutoff molecular weight of 3500 Da.

The ethanol used during ethanol precipitation treatment, is preferably the ethanol aqueous solution in a preferable volume percentage of 70-95%.

Concentration can be carried out in the concentration manner in many prior art, in which vacuum concentration is optimal. The temperature during vacuum concentration is preferably 40° C.

The *Cistanche deserticola* polysaccharide according to the present invention, can be orally administered directly, and can also be formulated into many pharmaceutical dosage forms, such as capsule, tablet, powder, granule or oral liquid etc., after oral administration, it has an efficacy of supplementary for inhibiting colon cancer tumor.

Thus, the dosage form of the functional food of the present invention is preferably capsule, tablet, powder, granule or oral liquid etc.

In view of the prior art, the present invention has the following advantages:

(1) The *Cistanche deserticola* polysaccharide according to the present invention, with a high purity and activity, is able to regulate tumor microenvironment by many pathways such as inhibiting tumor angiogenesis, immunosuppression, anti-oxidation and inhibiting the growth of colon cancer fibroblast, it has a good effect of supplementary for inhibiting colon cancer tumor;

(2) The preparation method of *Cistanche deserticola* polysaccharide according to the present invention, is simple, stable and efficient in the process, suitable for industrial production and economic;

(3) The *Cistanche deserticola* polysaccharide according to the present invention, can be used for the preparation of functional food having efficacy of supplementary for inhibiting colon cancer tumor.

DETAILED DESCRIPTION OF PARTICULAR EMBODIMENTS OF THE INVENTION

Figure 1:
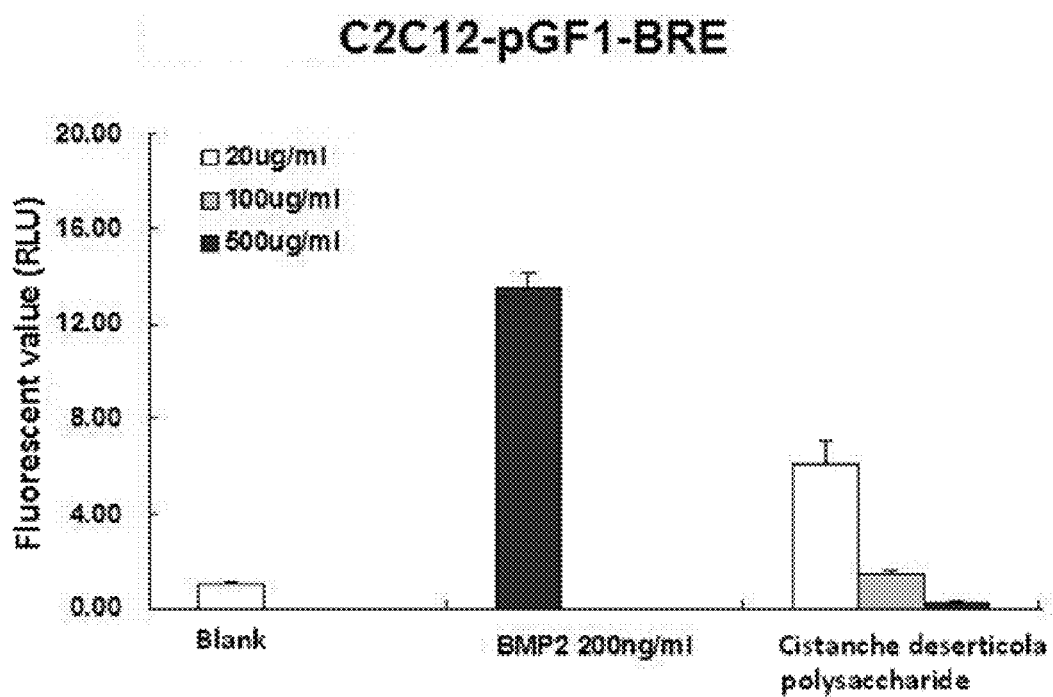
FIG. 1 demonstrates the activity of *Cistanche deserticola* polysaccharide in Example 4 of the present invention for inhibiting BRE reporter gene-carrying luciferase induced by BMP2.

The present invention will be further demonstrated by attached figures and Examples hereinbelow, while the present invention is not restricted in any form.

All the raw materials used in the following Examples, if not specified, are commercially available products.

Example 1

The *Cistanche deserticola* polysaccharide in this example, is prepared by the following method: *Cistanche deserticola* raw material is used for extraction with boiling water, during the first extraction, the administration amount of water is 20 folds of the total mass of raw material, boiled for 5 h and filtered; during the second extraction, the administration amount of water is 20 folds of the total mass of raw material, boiled for 3 h and filtered; during the third extraction, the administration amount of water is 10 folds of the total mass of raw material, boiled for 2 h and filtered, the filtrates are combined, is vacuum concentrated to around ⅟₁₀ of the original volume, sic passim. Concentrate liquid is processed with deproteinization treatment with trichloroacetic acid, the same volume (sic passim) of 30% (mass percentage) trichloroacetic acid is added, after a treatment duration of 4 h, neutralized with 10% (mass percentage) NaOH, sic passim, after neutralization, reaction liquid is placed into dialysis bag to carry on bag-sealed dialysis, the cutoff molecular weight of dialysis bag during dialysis is generally around 3500 Da, sic passim, then the liquid in the dialysis bag is concentrated, centrifuged, 85% (volume percentage) ethanol aqueous solution in a 3-4 folds volume is added to the supernatant to carry on ethanol precipitation treatment, upon treatment including vacuum drying (about 40° C., sic passim) of precipitate, *Cistanche deserticola* polysaccharide component is obtained.

Example 2

The *Cistanche deserticola* polysaccharide in this example, is prepared by the following method: *Cistanche deserticola* raw material is used for extraction with boiling water, during the first extraction, the administration amount of water is 15 folds of the total mass of *Cistanche deserticola* raw material, boiled for 5 h and filtered; during the second extraction, the administration amount of water is 15 folds of the total mass of *Cistanche deserticola* raw material, boiled for 3 h and filtered; during the third extraction, the administration amount of water is 10 folds of the total mass of *Cistanche deserticola* raw material, boiled for 3 h and filtered, the filtrates are combined, and vacuum concentrated. Concentrate liquid is processed with deproteinization treatment with trichloroacetic acid, the same volume of 25% (mass percentage) trichloroacetic acid is added, after a treatment duration of 3 h, neutralized with 10% (mass percentage) NaOH, after neutralization, reaction liquid is placed into dialysis bag to carry on bag-sealed dialysis, then the liquid in the dialysis bag is concentrated, centrifuged, 70% (volume percentage) ethanol aqueous solution in a 3-4 folds volume is added to the supernatant to carry on ethanol precipitation treatment, upon treatment including vacuum drying of precipitate, *Cistanche deserticola* polysaccharide component is obtained.

Example 3

The *Cistanche deserticola* polysaccharide in this example, is prepared by the following method: *Cistanche deserticola* raw material is used for extraction with boiling water, during the first extraction, the administration amount of water is 10 folds of the total mass of *Cistanche deserticola* raw material, boiled for 3 h and filtered; during the second extraction, the administration amount of water is 20 folds of the total mass of *Cistanche deserticola* raw material, boiled for 3 h and filtered; during the third extraction, the administration amount of water is 10 folds of the total mass of *Cistanche deserticola* raw material, boiled for 5 h and filtered, the filtrates are combined, and vacuum concentrated, concentrate liquid is processed with deproteinization treatment with trichloroacetic acid, the same volume of 15% (mass percentage) trichloroacetic acid is added, after a treatment duration of 5 h, neutralized with 10% (mass percentage) NaOH, after neutralization, reaction liquid is placed into dialysis bag to carry on bag-sealed dialysis, then the liquid in the dialysis bag is concentrated, centrifuged, 95% (volume percentage) ethanol aqueous solution in a 3-4 folds volume is added to the supernatant to carry on ethanol precipitation treatment, upon treatment including vacuum drying of precipitate, *Cistanche deserticola* polysaccharide component is obtained.

Example 4

Activity of *Cistanche deserticola* Polysaccharide for Inhibiting BRE Reporter Gene-Carrying Luciferase Induced by BMP2

C2C12 cell strain is purchased from the cell bank of Chinese Academy of Science (CAS), C2C12-pGF1-BRE cell strain is constructed by Dingkan Lab in Shanghai Institute of Materia Medica, CAS, and conserved in liquid nitrogen. C2C12-pGF1-BRE cell is cultivated in the DMEM medium comprising 10% Gibco fetal bovine serum, placed in an incubator having a saturated humidity at 37° C. and comprising 5% $CO_2$ to be cultivated, is inoculated in a density of $1\times10^4$ cell/well into a 96-well plate, 100 μL each well. After attaching for 24 h, 60 μL of medium is sucked, and replaced by 50 μL of sample (*Cistanche deserticola* polysaccharide in Example 1) prepared to be corresponding concentration, with a final concentration of 0.5 mg/mL, 0.1 mg/mL, 0.02 mg/mL, respectively, 10 μL of BMP2 is added to adjust to the final concentration of 200 ng/mL. Meanwhile, Blank group and BMP2 control group are set. After an administration of 16 h, medium is sucked, and replaced by 20 μL of Reporter Lysis 1× Buffer, 20 μL of the lysis solution of lytic cells is transferred to blank plate, 40 μL luciferase substrate is added, the plate is read in 3 min, RLU value is obtained. Statistical analysis is processed using SPSS statistical software. Each data is represented by mean±standard deviation (.x±s), the comparison between two groups is carried out by independent sample t test, the comparison among many groups is carried out by one-way ANOVA.

The experiment results are as shown in FIG. 1, *Cistanche deserticola* polysaccharide in a low concentration of 0.02 mg/mL, has the activity for inhibiting BRE reporter gene-carrying luciferase induced by BMP2, and said activity increases significantly as the concentration of polysaccharide increases, which demonstrates that said polysaccharide has dose-dependency with respect to the activity. It is known that tumor angiogenesis plays a crucial role during the occurrence and development process of tumor, and the BMP2 signalling pathway plays a crucial role during the tumor angiogenesis processes. Said polysaccharide can inhibit BMP2 signalling pathway significantly, which demonstrates that said polysaccharide has the efficacy of regulating tumor microenvironment.

Example 5

Activity of *Cistanche deserticola* Polysaccharide for Inhibiting the Reporter Gene Carrying SMAD2/3/4 Induced by TGFβ

HEK293 T cell strain is purchased from the cell bank of CAS, HEK293T-pGF1-SMAD2/3/4 cell strain is constructed by Dingkan Lab in Shanghai Institute of Materia Medica, CAS, and conserved in liquid nitrogen. HEK293T-pGF1-SMAD2/3/4 cell is cultivated in the DMEM medium comprising 10% Gibco fetal bovine serum, placed in an incubator having a saturated humidity at 37° C. and comprising 5% $CO_2$ to be cultivated, is inoculated in a density of $2\times10^4$ cell/well into a 96-well plate, 100 μL each well. After attaching for 24 h, 60 μL of medium is sucked, and replaced by 50 μL of sample (*Cistanche deserticola* polysaccharide in Example 1) prepared to be corresponding concentration, with a final concentration of 0.5 mg/mL, 0.1 mg/mL, 0.02 mg/mL, respectively, 10 μL of TGFβ1 is added to adjust to the final concentration of 50 ng/mL. Meanwhile, Blank group and TGFβ1 control group are set. After an administration of 16 h, medium is sucked, and replaced by 20 μL of Reporter Lysis 1× Buffer, 20 μL of the lysis solution of lytic cells is transferred to blank plate, 40 μL luciferase substrate is added, the plate is read in 3 min, RLU value is obtained. Statistical analysis is processed using SPSS statistical software. Each data is represented by mean±standard deviation (.x±s), the comparison between two groups is carried out by independent sample t test, the comparison among many groups is carried out by one-way ANOVA.

Figure 2:
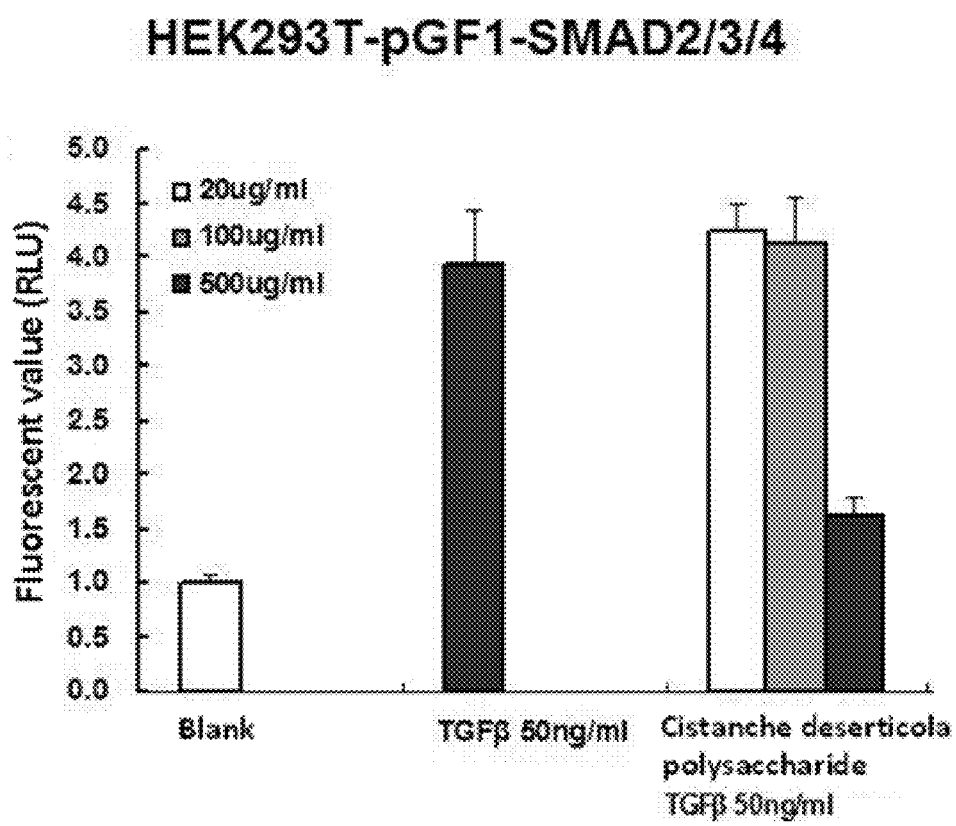
FIG. 2 demonstrates the activity of *Cistanche deserticola* polysaccharide in Example 5 of the present invention for inhibiting the reporter gene carrying SMAD2/3/4 induced by TGFβ.

The experiment results are as shown in FIG. 2, *Cistanche deserticola* polysaccharide in a concentration of 0.5 mg/mL, has the activity for inhibiting the signalling pathway carrying SMAD2/3/4 induced by TGFβ. It is known that tumor angiogenesis plays a crucial role during the occurrence and development process of tumor, and the TGFβ induced SMAD2/3/4 signalling pathway plays a crucial role during the tumor angiogenesis processes. Said polysaccharide can inhibit the signalling pathway significantly, which demonstrates that said polysaccharide has the efficacy of regulating tumor microenvironment.

Example 6

Activity of *Cistanche deserticola* Polysaccharide for Activating NF-κB Reporter Gene-Carrying Luciferase THP-1 cell strain is purchased from the cell bank of CAS, THP-1/pGF1-NF-κB cell strain is constructed by Dingkan Lab in Shanghai Institute of Materia Medica, CAS, and conserved in liquid nitrogen. THP-1/pGF1-NF-κB cell is cultivated in the RPMI-1640 medium comprising 10% fetal bovine serum, placed in an incubator having a saturated humidity at 37° C. and comprising 5% $CO_2$ to be cultivated, is inoculated in a density of $5\times10^4$ cell/well into a 96-well plate, a volume of 50 μL each well. 50 μL of the test sample (*Cistanche deserticola* sample in Example 1) is added, with a final concentration of 0.5 mg/mL, 0.1 mg/mL, 0.02 mg/mL, respectively, Meanwhile, Blank group and LPS control group are set. 10 μL of LPS solution is added, in a final concentration of 1 μg/mL, placed in an incubator having a saturated humidity at 37° C. and comprising 5% $CO_2$ to be cultivated overnight. After overnight cultivation, 100 μL of Bright-Glo™ Luciferase Assay System substrate is added to each well, the plate is read on a microplate reader, RLU value is obtained.

$$\text{Activation rate}(\%) = \frac{RLU(LPS) - RLU(\text{Compound})}{RLU(LPS) - RLU(\text{Blank})} \times 100\%$$

Statistical analysis is processed using SPSS statistical software. Each data is represented by mean±standard deviation (.x±s), the comparison between two groups is carried out by independent sample t test, the comparison among many groups is carried out by one-way ANOVA.

Figure 3:
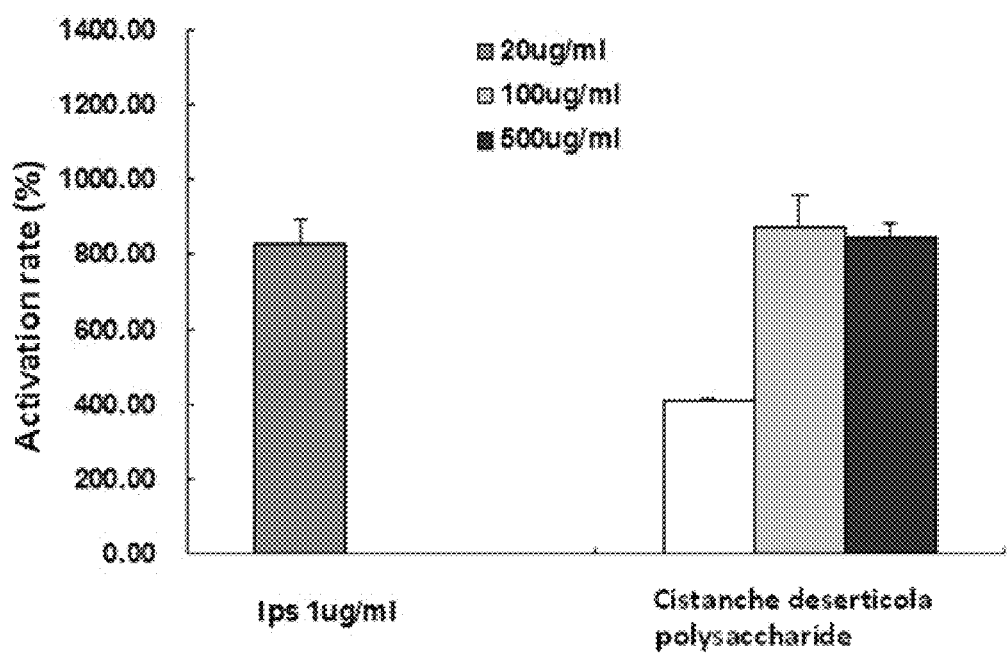
FIG. 3 demonstrates the activity of *Cistanche deserticola* polysaccharide in Example 6 of the present invention for activating NF-κB reporter gene-carrying luciferase.

The experiment results are as shown in FIG. 3, said polysaccharide in the low concentrations of 0.1 mg/mL and 0.5 mg/mL, has quite good activity for activating NF-κB signalling pathway. After activation of NF-κB, organism immunity can be enhanced, which indirectly carry on anti-tumor effects.

Example 7

Activity of *Cistanche deserticola* Polysaccharide for Inhibiting HRE Reporter Gene-Carrying Luciferase Induced by $Cocl_2$ HEK293T cell strain is purchased from the cell bank of CAS, HEK293T-pGF1-HRE cell strain is constructed by Dingkan Lab in Shanghai Institute of Materia Medica, CAS, and conserved in liquid nitrogen. HEK293T-pGF1-HRE cell is cultivated in the DMEM medium comprising 10% Gibco fetal bovine serum, inoculated in a density of $2 \times 10^4$ cell/well into a 96-well plate, 100 μL each well. After attaching for 24 h, 60 μL of medium is sucked, and replaced by 50 μL of sample (*Cistanche deserticola* polysaccharide in Example 1) prepared to be corresponding concentration, with a final concentration of 0.5 mg/mL, 0.1 mg/mL, 0.02 mg/mL, respectively, 10 μL of $Cocl_2$ is added to adjust to the final concentration of 250 μM. Meanwhile, Blank group and $Cocl_2$ control group are set. After an administration of 16 h, medium is sucked, and replaced by 20 μL of Reporter Lysis 1× Buffer, frozen in an −80° C. refrigerator till plate reading. The plate to be read is removed from the −80° C. refrigerator, 20 μL of the lysis solution of lytic cells is transferred to blank plate, 40 μL luciferase substrate is added, the plate is read in 3 min, RLU value is obtained. Statistical analysis is processed using SPSS statistical software. Each data is represented by mean±standard deviation (.x±s), the comparison between two groups is carried out by independent sample t test, the comparison among many groups is carried out by one-way ANOVA.

Figure 4:
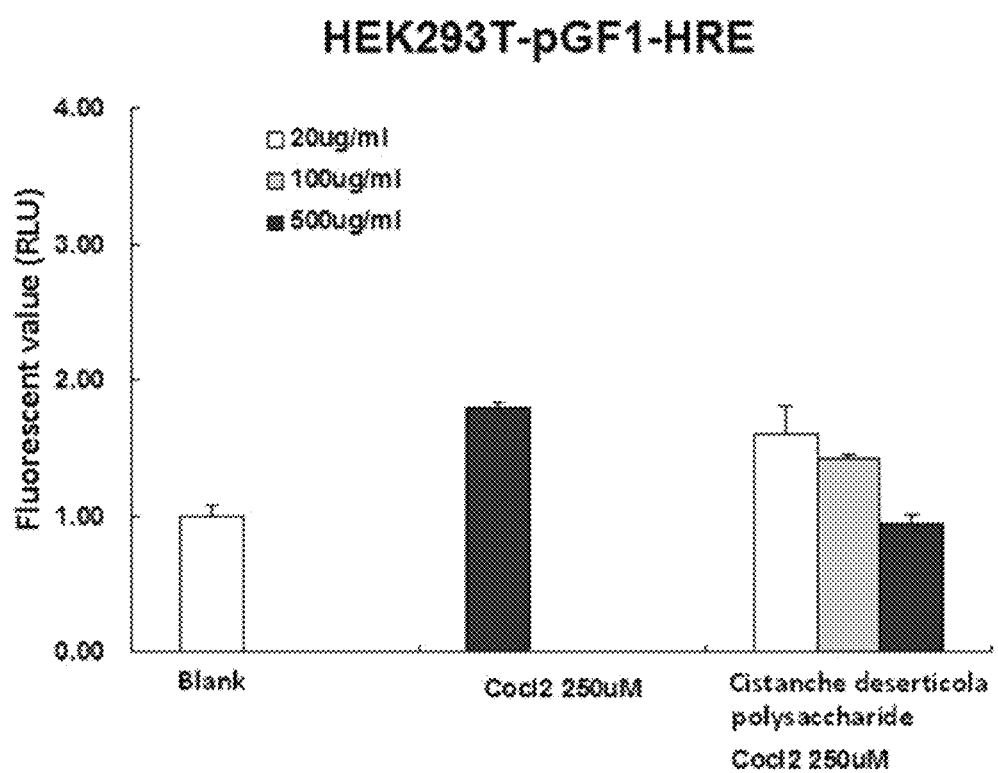
FIG. 4 demonstrates the activity of *Cistanche deserticola* polysaccharide in Example 7 of the present invention for inhibiting HRE reporter gene-carrying luciferase induced by $CoCl_2$.

The activity assay results of *Cistanche deserticola* polysaccharide are as shown in FIG. 4, *Cistanche deserticola* polysaccharide in a concentration of 0.5 mg/mL, may inhibit the activity of HRE reporter gene-carrying luciferase induced by $Cocl_2$, which proves that it has potential antioxidation activity.

Example 8

*Cistanche deserticola* Polysaccharide can Inhibit the Growth of Colon Cancer CT26-CAF Tumor-related fibroblast cell line CT26-CAF is constructed by Institute of Biophysics, CAS. Cells are inoculated into a 96-well plate in a cell density of $1 \times 10^4$/well. *Cistanche deserticola* polysaccharide in Example 1 is dissolved in DMEM+/+ medium, to make its concentration to be 1.0 mg/mL. Cultivated for 4d, CCK assay kit (Beijing Zoman Biotechnology Co., Ltd.) is used to detect the growth status of cell. The sample of each polysaccharide is in triplicate.

Statistical analysis: the comparison among data from many groups is calculated by ANOVA, firstly, the data is processed with homogeneity of variance test, the Levene Statistical value is calculated, if variance is homogenous, multiple comparison among groups is carried on, the test is LSD and Dunnett, if variance is non-homogenous, Dunnett t correction method is used. Statistical software is SPSS17.0, the significance level is α=0.05.

Figure 5:
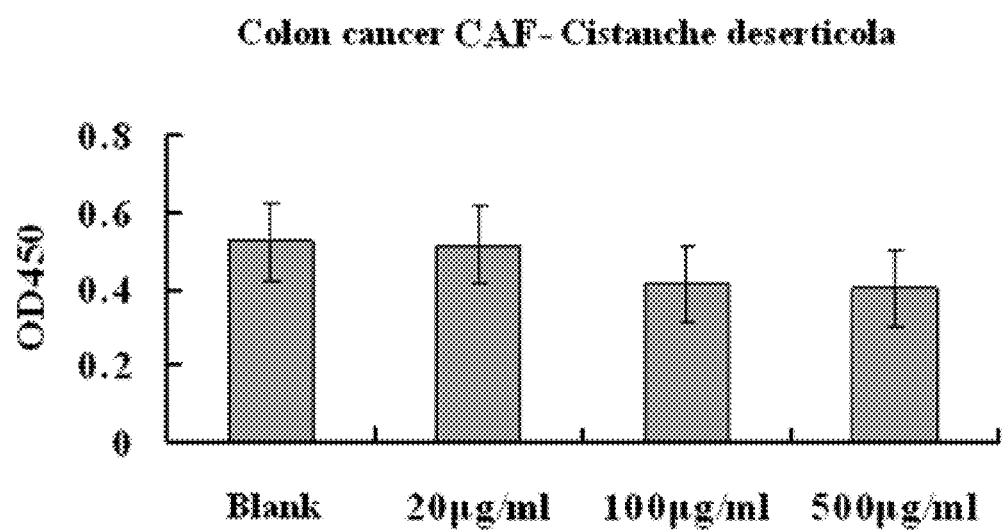
FIG. 5 demonstrates *Cistanche deserticola* polysaccharide in Example 8 of the present invention for inhibiting the growth of colon cancer fibroblasts.

The experiment results are as shown in FIG. 5, the *Cistanche deserticola* polysaccharide, in a concentration of 0.5 mg/mL, can inhibit the growth of colon cancer CT26-CAF significantly. CT26-CAF has an important regulation role for colon cancer, can promote the growth of colon cancer cells. Said polysaccharide can carry on the efficacy of regulating colon cancer microenvironment by inhibiting growth of colon cancer CT26-CAF. Currently, CAF is becoming the target of tumor therapy. Further researches discover that, clearing the CAF in the tumor microenvironment, has efficacy of resulting in the extinction of certain tumors, therefore, by regulating tumor microenvironment, the polysaccharide demonstrates potential supplementary anti-tumor value.

The aforesaid experiments prove that the *Cistanche deserticola* polysaccharide according to the present invention can regulate tumor microenvironment by many pathways such as inhibiting tumor angiogenesis, immunosuppression, antioxidation and inhibiting the growth of colon cancer fibroblast, and further carry on potential activity against colon cancer tumor, thus *Cistanche deserticola* polysaccharide can be formulated into many pharmaceutical dosage forms by conventional processes, to prepare the functional food having efficacy of supplementary for inhibiting colon cancer, the dosage forms of functional food can be capsule, tablet, powder, granule or oral liquid etc.

The aforesaid examples are preferable embodiments of the present invention, but the embodiments of the present invention are not limited by the aforesaid examples, any other change, modification, substitution, combination, abbreviation made not departing from the spirit essence and principle of the present invention, is regarded as equivalent substitution manner, and are enclosed within the protection scope of the present invention.

What is claimed is:

1. A method of inhibiting angiogenesis for regulating colon cancer tumor microenvironment by ingesting a food supplement containing *Cistanche deserticola* polysaccharide, which is specifically prepared by a processes including extraction with boiling water, deproteinization, dialysis and ethanol treatment, where the dialysis is performed with a dialysis bag of a cutoff molecular weight of 3500 Da.

2. The method according to claim 1, wherein the extraction with boiling water is carried out for 1-5 times each with boiling water of 5-20 folds of the total mass of *Cistanche deserticola* for a duration of 1.5-5 h.

3. The method according to claim 1, wherein 35% (v/v) trichloroacetic acid aqueous solution is used for deproteinization, and the deproteinization duration is 3-6 h.

4. The method according to claim 1, wherein *Cistanche deserticola* as raw material is extracted with boiling water for a plurality of times with resulting extract liquids combined, and concentrated to obtain a concentrated liquid, to which a trichloroacetic acid aqueous solution is added to perform deproteinization and then ethanol aqueous solution 70-95% (v/v) is added to perform the ethanol treatment.

5. The method according to claim 1, wherein the food supplement is in a dosage form of capsule, tablet, powder, granule or oral liquid.

* * * * *